(12) United States Patent
Kidooka

(10) Patent No.: US 7,354,439 B2
(45) Date of Patent: Apr. 8, 2008

(54) TREATMENT TOOL FOR ENDOSCOPE HAVING END EFFECTOR OPERATING LIKE PINCERS

(75) Inventor: Satoshi Kidooka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 192 days.

(21) Appl. No.: 10/616,970

(22) Filed: Jul. 11, 2003

(65) Prior Publication Data
US 2004/0015165 A1 Jan. 22, 2004

(30) Foreign Application Priority Data
Jul. 17, 2002 (JP) ............................. 2002-207777

(51) Int. Cl.
*A61B 18/18* (2006.01)
(52) U.S. Cl. ....................................................... 606/51
(58) Field of Classification Search ........ 606/207–208, 606/1, 27–52, 205
See application file for complete search history.

(56) References Cited

U.S. PATENT DOCUMENTS

| 5,482,054 | A | * | 1/1996 | Slater et al. ................. 600/564 |
| 5,853,412 | A | * | 12/1998 | Mayenberger ................ 606/51 |
| 6,050,996 | A | * | 4/2000 | Schmaltz et al. ............. 606/51 |
| 6,083,240 | A | | 7/2000 | Ouchi |
| 6,099,537 | A | | 8/2000 | Sugai et al. |
| 6,458,130 | B1 | | 10/2002 | Frazier et al. |
| 6,582,451 | B1 | * | 6/2003 | Marucci et al. ............. 606/207 |
| 6,689,122 | B2 | | 2/2004 | Yamamoto |
| 6,776,780 | B2 | * | 8/2004 | Mulier et al. ................. 606/51 |

FOREIGN PATENT DOCUMENTS

| JP | 5-317246 | 12/1993 |
| JP | 8-140987 | 6/1996 |
| JP | 9-262243 | 10/1997 |
| JP | 2000-262534 | 9/2000 |
| JP | 2000-279420 | 10/2000 |
| JP | 2000-279421 | 10/2000 |
| JP | 3238638 | 10/2001 |
| JP | 2001-321386 | 11/2001 |
| JP | 2002-165754 | 6/2002 |
| JP | 2002-528167 | 9/2002 |
| JP | 2003-033366 | 2/2003 |

OTHER PUBLICATIONS

English language Abstract of JP 2002-528167.
English language Abstract of JP 2000-262534.
English language Abstract of JP 2001-321386.
English language Abstract of JP 2003-033366.

* cited by examiner

*Primary Examiner*—Roy D. Gibson
*Assistant Examiner*—Pete Vrettakos
(74) *Attorney, Agent, or Firm*—Greenblum & Bernstein, P.L.C.

(57) ABSTRACT

A bipolar high frequency treatment tool includes an inserting portion to be inserted into a human body through an instrument channel of the endoscope. An electrode assembly is attached to the distal end of the inserting portion. The electrode assembly includes a supporting member having a slit, a pair of shafts held by the supporting member so as to cross the slit, and a pair of electrodes. The pair of electrodes is pivotably supported by the pair of shafts so as to open and close like a pair of pincers. An insulator block is located in the slit between the pair of electrodes to prevent the pair of electrodes from making a short circuit within the slit. The pair of shafts is pressed into the insulating block so that the shafts do not come of from the insulating block and hence from the supporting member.

21 Claims, 7 Drawing Sheets

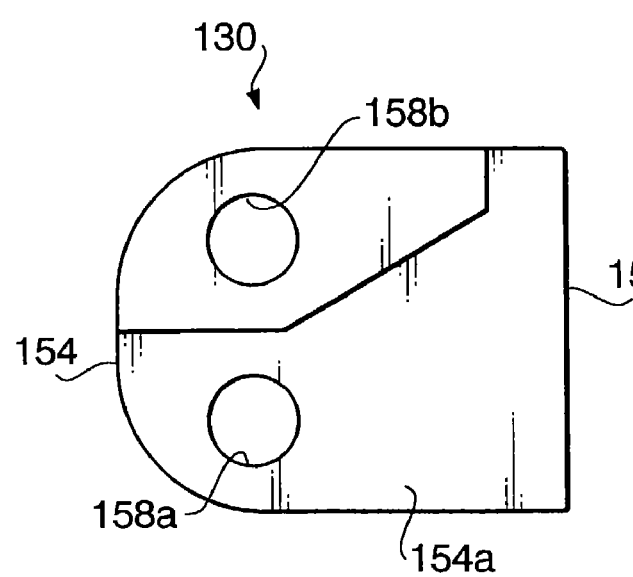
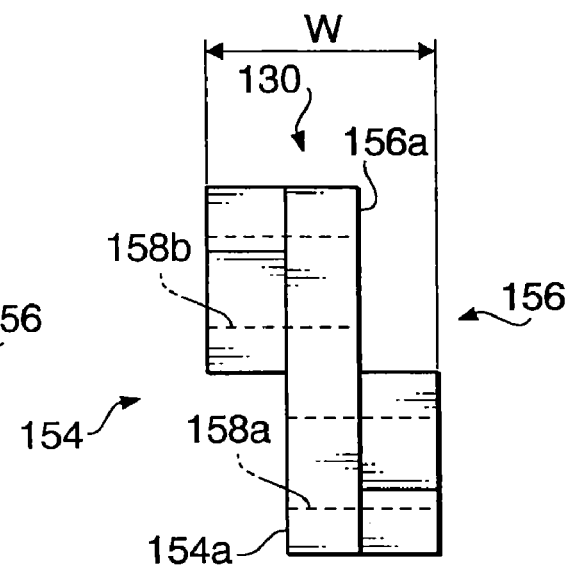
FIG.7A   FIG.7B
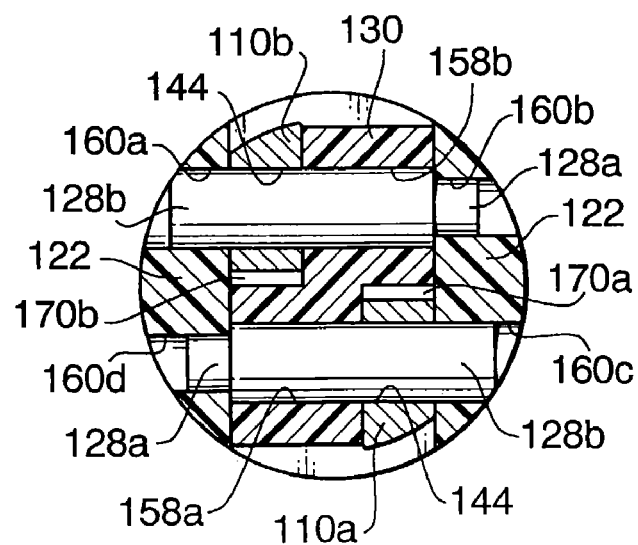
FIG. 8

TREATMENT TOOL FOR ENDOSCOPE HAVING END EFFECTOR OPERATING LIKE PINCERS

BACKGROUND OF THE INVENTION

The present invention relates to a treatment tool for an endoscope, which is provided with an end effector including a pair of manipulation members pivotably supported at the distal end of the treatment tool so as to operate like pincers.

Treatment tools for endoscopes having end effectors operating like pincers include a biopsy forceps, a grasping forceps, a hemosatic forceps, a pinching forceps, or the like.

FIG. 1 shows a distal end portion of a conventional treatment tool provided with an end effector that operates like pincers. The conventional treatment tool has a flexible sheath 1 and a supporting member 2 attached to the distal end of the sheath 1. The supporting member 2 is provided with a slit 3 having a constant width. A supporting shaft 5 is held at the distal end of the slit 3 so as to cross the slit 3 in the width direction thereof.

A pair of manipulation members 4 is pivotably mounted on the supporting shaft 5. The proximal end portions of the manipulation members 4 are connected to a pair of operation wires 6 which are passed through the sheath 1. The pair of operation wires is advanced/retracted along the sheath 1 to open and close the pair of manipulation members 4 like a pair of pincers.

The supporting shaft 5 is mounted to the supporting member 2 by inserting it into a pair of through holes 10 formed to the supporting member 2 on both sides of the slit 3. Since the head of the supporting shaft 5 is formed in a diameter larger that the remaining part thereof, the supporting shaft 5 does not pass through the through holes 10. After being inserted into the through holes 10, the supporting shaft 5 is secured to the supporting member 2 by swaging the tip end thereof.

The supporting shaft 5 arranged as above does not come off from the supporting member 2 even if a large force is exerted thereon in a direction from the head toward the tip end thereof since the large diameter head of the supporting shaft 5 cannot pass through the holes 10. On the contrary, since the swaged tip end of the supporting shaft 5 may be deformed relatively easily, the supporting member may drop out from the supporting member 2 if it is pulled or pushed in a direction from tip end toward the head thereof, resulting in disassembling of the tip end of the treatment tool.

In order to make the supporting member insulative, the supporting member 2 is often made of non-metallic material. In such a case, the tip end of the supporting shaft 5 cannot be swaged with a large force since it may break the supporting member 2 having lower mechanical strength compared to those made of metal. As a result, the supporting shaft 5 tends to be swaged insufficiently and becomes more easily to drop off from the supporting member 2.

Therefore, there is a need for a treatment tool in which a supporting shaft for pivotally supporting a manipulation member does not easily come off from the treatment tool.

SUMMARY OF THE INVENTION

The present invention is advantageous in that a treatment tool for an endoscope that satisfies the above-mentioned need is provided.

According to an aspect of the invention, there is provided a treatment tool to be inserted into a human body through an endoscope. The treatment tool includes an elongated inserting portion to be inserted through an accessory channel of the endoscope. A supporting member is attached to a distal end of the inserting portion. The supporting member is provided with a slit. A shaft is attached to the supporting member so as to cross the slit in the width direction thereof. A pair of manipulation members is pivotably supported by the shaft within the slit so as to open and close like a pair of pincers. A spacer is located between the pair of manipulation members to keep the manipulation members spaced apart from each other within the slit. The shaft is supported by the spacer so as not to come off from said supporting member.

In the treatment tool configured as described above, it is not necessary to swage the end portions of the shaft in order to secure the shaft to the supporting member since the spacer prevents the shaft from coming off from the supporting member. Thus, the shaft and hence the pair of manipulation members do not easily come off from the supporting member due to deformation of any swaged portion.

Optionally, the shaft may be pressed into said spacer so as to be tightly fit thereinto. In an exemplary embodiment of the invention, the spacer is provided with a through hole having an inner diameter smaller than an outer diameter of the shaft, and the shaft is pressed into the through hole.

Optionally, the treatment tool may include a pair of the above-mentioned shafts both of which are pressed into the spacer, and each of the pair of manipulation members may be pivotably mounted to respective one of the shafts so as to open and close like a pair of pincers. In an exemplary embodiment of the invention, the spacer is provided with a pair of through holes formed in parallel to each other and having inner diameters smaller than the outer diameters of the shafts, and the shafts is pressed into respective one of the through holes.

In some cases, the pair of manipulation members are a pair of electrodes, and the spacer insulates the electrodes from each other. The spacer may be made of poly-tetra-fluoro-ethylene or ceramic, for example.

In the above-mentioned case, the manipulation members may be arranged to be connectable to a high frequency power supply.

Optionally, the supporting member is made of insulating material.

BRIEF DESCRIPTION OF THE ACCOMPANYING DRAWINGS

FIG. 1 is a perspective view of a conventional treatment tool for an endoscope;

FIG. 2 schematically shows a bipolar high frequency treatment tool according to an embodiment of the invention connected to a high frequency power supply;

FIGS. 7A and 7B show the right side and the rear side of an insulating block of the electrode assembly, respectively; and FIG. 8 is a sectional view of the electrode assembly taken along the line VIII-VIII in FIG. 4.

DETAILED DESCRIPTION OF THE EMBODIMENTS

Hereinafter, an embodiment of the invention will be described with reference to the accompanying drawings.

Figure 1:
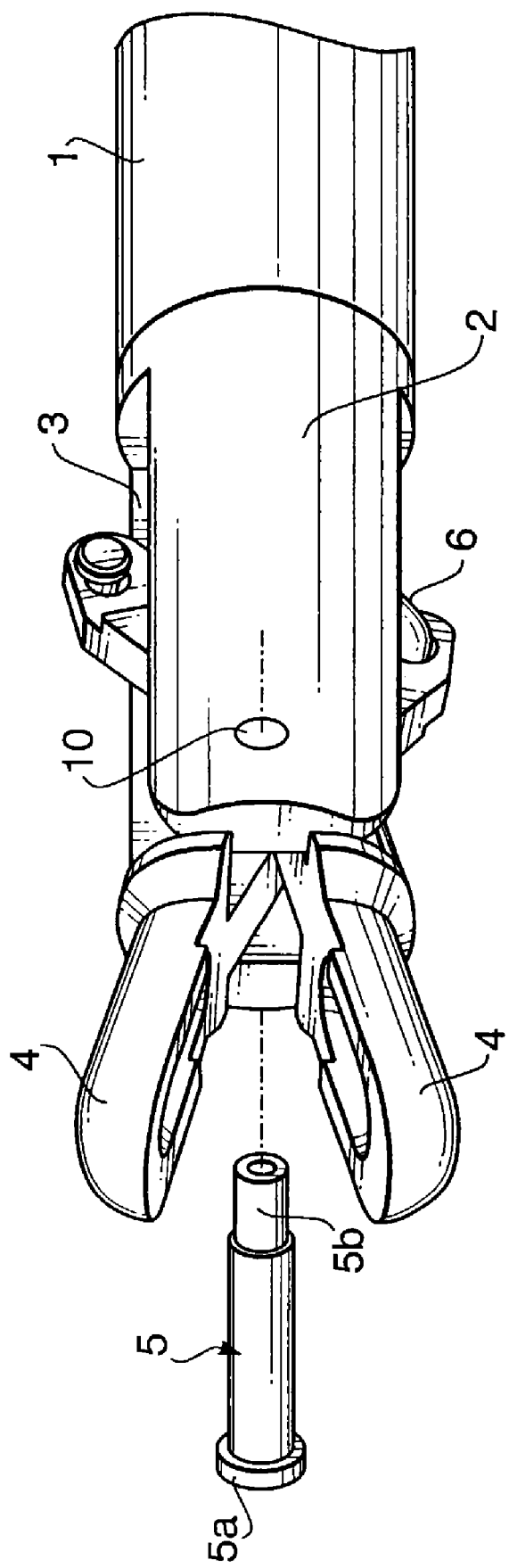
Figure 2:
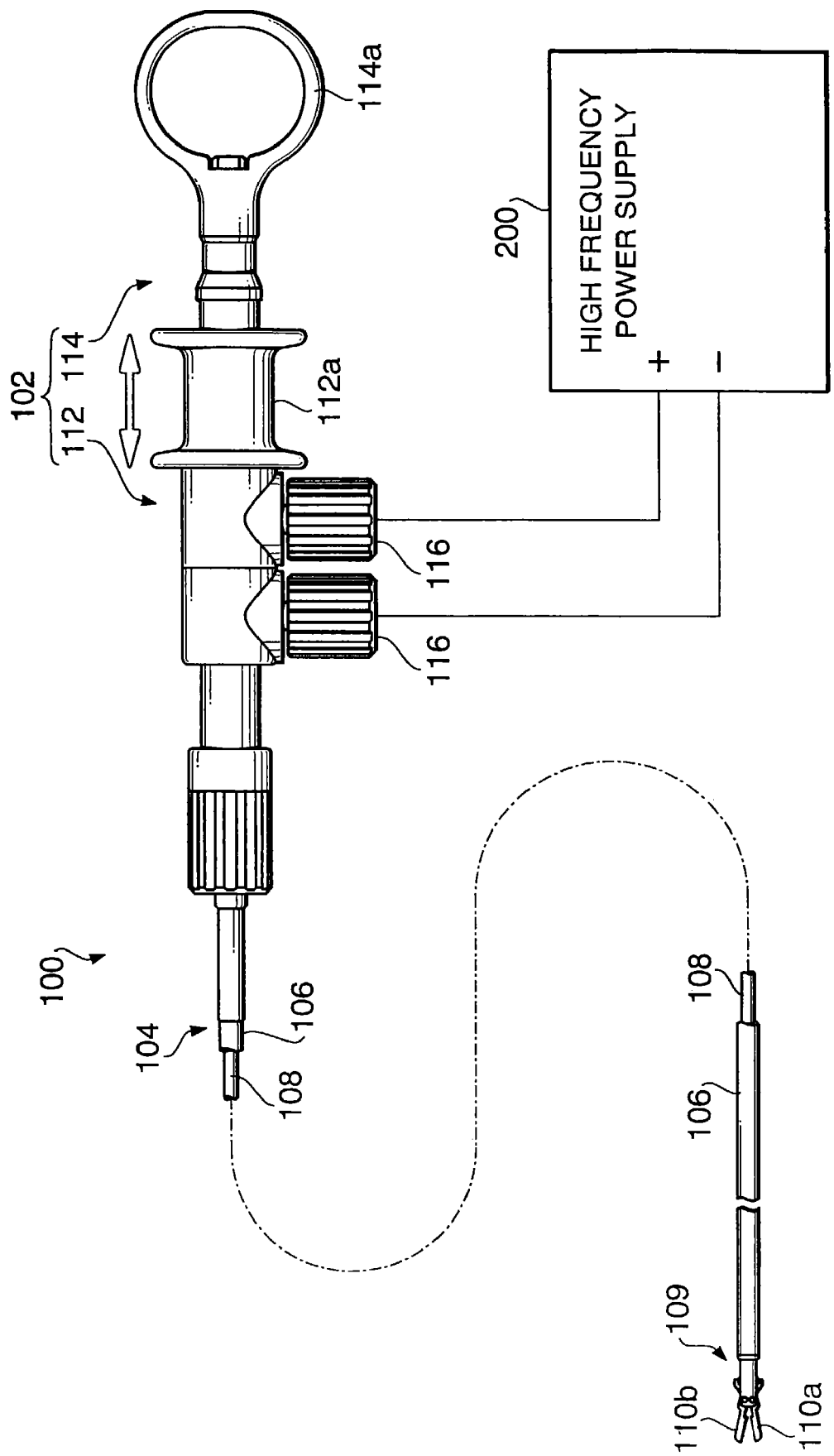

FIG. 2 schematically shows a bipolar high frequency treatment tool 100 according to an embodiment of the invention connected to a high frequency power supply 200.

The treatment tool 100 includes an operation portion 102 and an inserting portion 104 connected to the distal end of the operation portion 102.

The inserting portion 104 is provided in a form and size that allows it to be introduced into a body cavity through an accessory channel of an endoscope (not shown). The inserting portion 104 includes an elongated and flexible sheath 106, and a pair of conductive wires 108 (only one is shown) slidably passed through the sheath 106. The sheath 106 is made of insulating material such as poly-tetra-fluoro-ethylene (PTFE). In an exemplary embodiment, the sheath 106 is 1 m to 2 m long and has an outer diameter of 2 mm to 3 mm.

An electrode assembly 109 is mounted to the distal end of the insertion portion 104. The electrode assembly 109 includes an end effector, or first and second electrodes (manipulation members) 110a and 110b that are connected to the conductive wires 108.

The operating portion 102 includes a cylindrical portion 112 and a rod portion 114 slidably inserted into the cylindrical portion 112.

The cylindrical portion 112 has a circumferential groove 112a at a proximal end thereof. A user of the treatment tool 100 can hold the operation portion 112 by pinching it at the groove 112a with his index finger and long finger.

The rod portion 114 has a ring 114a into which the user can insert his thumb to slide the rod portion 114 within the cylindrical portion 112 back and forth.

The rod portion 114 is connected with the pair of wires 108 in the cylindrical portion 112 such that the wires 108 retract and proceed in the sheath 106 as the rod portion 114 is moved back and forth with respect to the cylindrical portion 112. It should be noted that the pair of wires 108 may be fixed to each other so that they slide integrally within the sheath 106 to move the pair of electrodes (110a, 110b) simultaneously.

The conductive wires 108 are detachably connected to power supply lines of the high frequency power supply 200 via a pair of connectors 116 provided to the side surface of the cylindrical portion 112. One of the conductive wires 108 is connected to the positive terminal of the power supply 200 and the other to the negative terminal.

Figure 3:
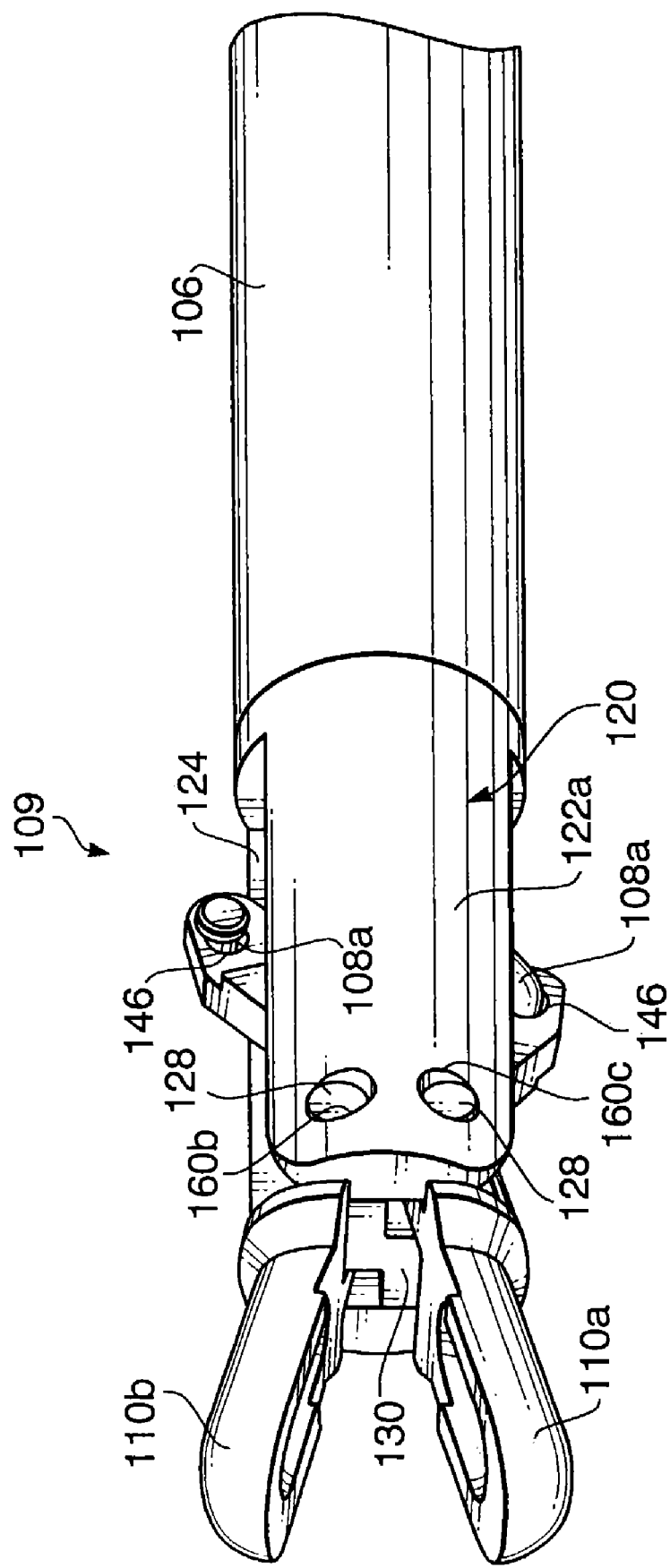
FIG. 3 is a perspective view of the distal end of the bipolar high frequency treatment tool shown in FIG. 2.
Figure 4:
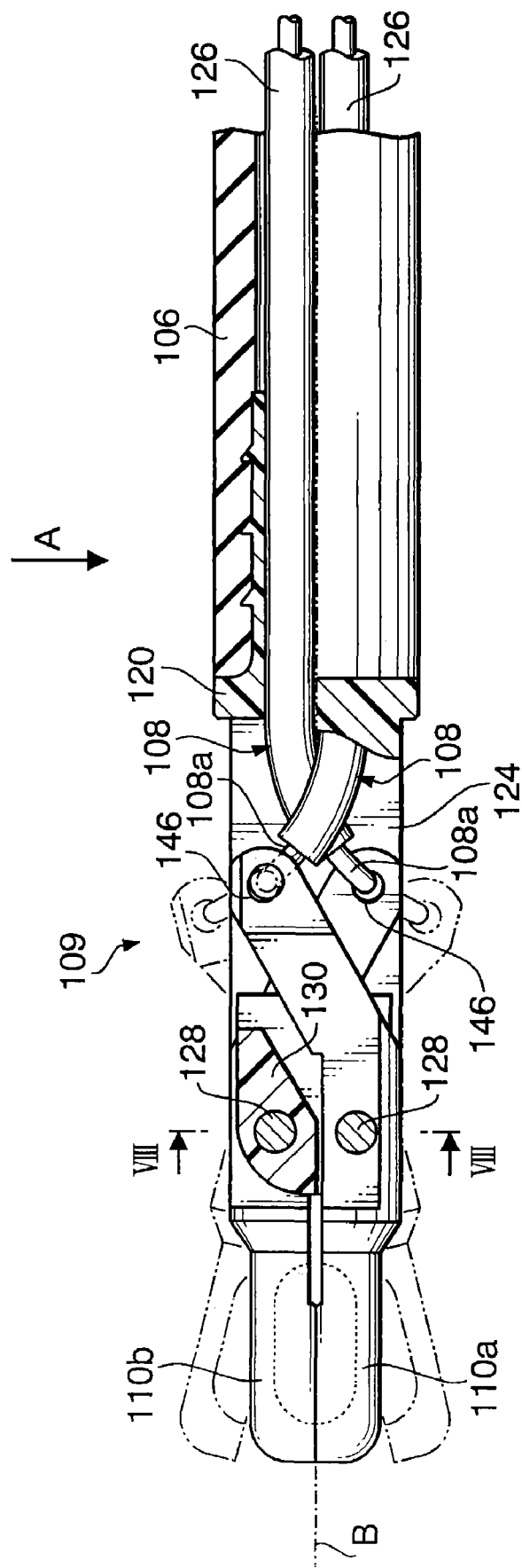
FIG. 4 is partially sectional side view of the distal end of the bipolar high frequency treatment tool shown in FIG. 2.
Figure 5:
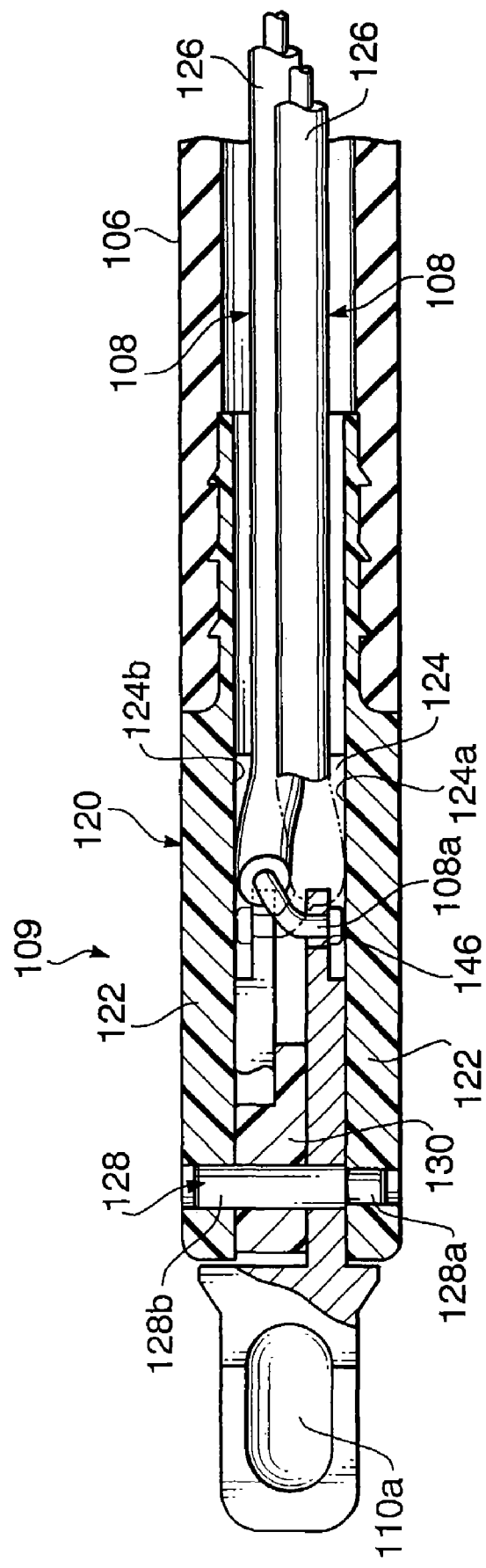
FIG. 5 is a sectional view of the distal end of the bipolar high frequency treatment tool observed from the direction indicated by the arrow A in FIG. 4.

FIG. 3 is a perspective view of the distal end of the treatment tool 100 shown in FIG. 2. FIG. 4 is partially sectional side view of the distal end of the treatment tool 100 shown in FIG. 2, and FIG. 5 is a sectional view of the distal end of the treatment tool 100 observed from the direction indicated by the arrow A in FIG. 4. Note that FIGS. 4 and 5 are drawn as a composite view combining cross sectional views at various positions.

The electrode assembly 109 includes a supporting member 120 for pivotably supporting the first and second electrodes 110a and 110b. The supporting member 120 is made of insulating material such as rigid plastic and ceramics and mounted to the distal end of the flexible sheath 106.

As shown in FIG. 5, the supporting member 120 has two arms 122 extending forwards and in parallel to each other to form a slit 124 therebetween having a constant width. A pair of shafts 128 is supported by the arms 122 in the vicinity of the distal end of the arms 122 so as to cross the slit 124 in the width direction thereof.

The pair of shafts 128 is held in parallel to and spaced apart from each other, and perpendicular to first and second inner side surfaces 124a and 124b of the slit 124. The shafts 128 are also located such that the center axis B of the supporting member 120 passes through therebetween. The shafts 128 are made of stainless steel, for example.

As best shown in FIG. 4, the first and second electrodes 110a and 110b are partially inserted into the slit 124 of the supporting member 120 and pivotably mounted to respective shafts 128. Thus, the electrodes 110a and 110b can open and close like a pair of pincers. That is, the electrodes 110a and 110b can move between a closed position as indicated by solid lines, at which the electrodes 110a and 110b come into contact with each other, and an open position as indicated by chain double-dashed lines, at which the electrodes 110a and 110b are located apart from each other.

The rear ends or proximal ends of the electrodes 110a and 110b are connected with the respective conductive wires 108. Each of the conductive wires 108 is covered with an insulating tube 126 except the end portion 108a thereof at which the conductive wire 108 is connected to the corresponding electrode (110a, 110b).

An insulating block 130 is provided in the slit 124 of the supporting member 120 to prevent the first and second electrodes 110a and 110b from coming into contact to each other within the slit 124. The insulating block 130 is located between the first and second electrodes 110a and 110b and supported by the pair of shafts 128.

Figure 6:
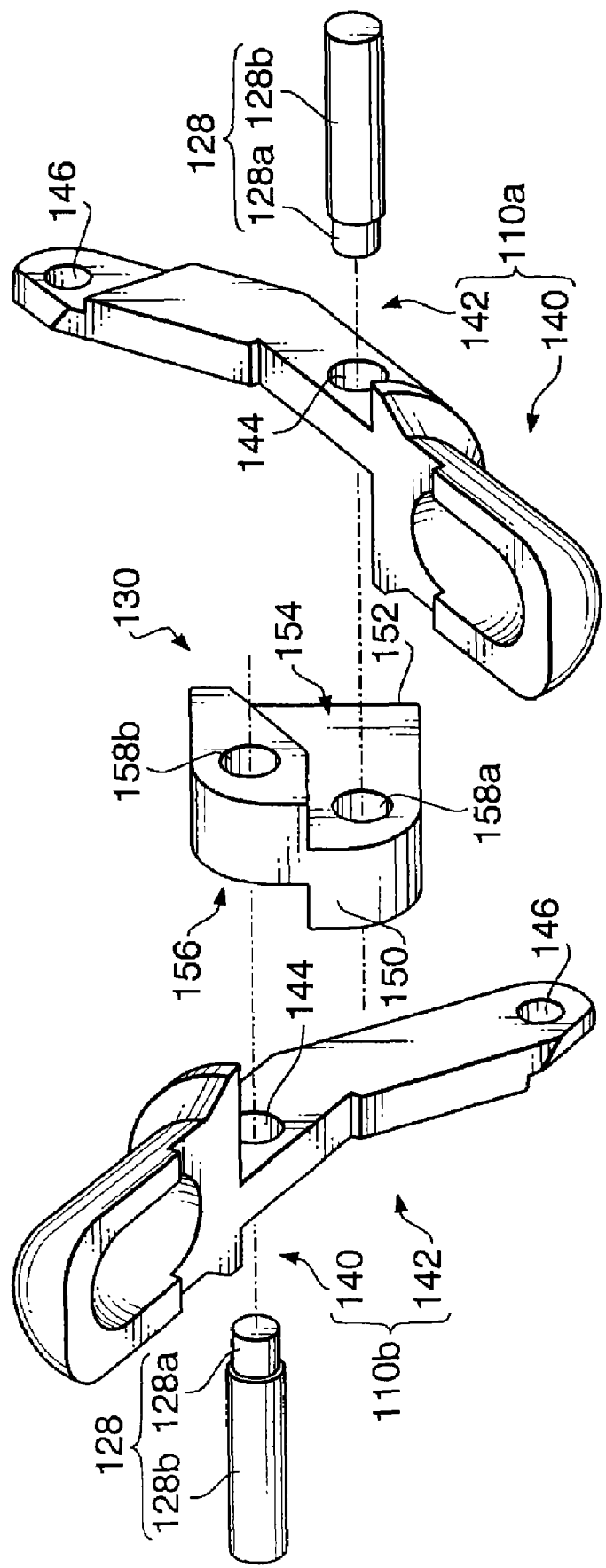
FIG. 6 is an exploded perspective view of an electrode assembly attached to the distal end of the treatment tool shown in FIG. 2.

FIG. 6 is an exploded perspective view of the electrode assembly 109. Note that the supporting member 120 is not shown in FIG. 6 for clarity of the drawing.

Each of the first and second electrodes 110a and 110b is an elongated member made of conductive metal such as stainless steel. Each electrode (110a, 110b) includes a front (distal) portion 140 and a rear (proximal) portion 142. When the electrodes 110a and 110b are mounted to the supporting member 120, the front portions 140 thereof are located outside of the slit 124 and the rear portions 142 thereof are located between the two arms 122.

Two through holes are formed to the rear portion 142 of each electrode (110a, 110b). The first one is a supporting hole 144 provided at substantially the center of each electrode (110a, 110b). The other one is a connection hole 146 formed in the vicinity of the rear end of each electrode (110a, 110b).

The first and second electrodes (110a, 110b) are pivotably mounted to the supporting member 120 by inserting the shafts 128 through the supporting holes 144 thereof.

The tip end of each conductive wire 108, which is exposed from the insulating tube 126, is passed through the connecting hole 146 and thereby connected with the corresponding electrode (110a, 110b).

The rear portion 142 of each electrode (110a, 110b) is slightly bent so that the conductive wires 108 sliding back and forth within the sheath 106 can swing the electrodes 110a and 110b around respective shafts 128 between the open and closed positions.

The front portion 140 of each electrode (110a, 110b) has a cup like shape. The electrodes 110a and 110b are arranged such that the cups like portions come in contact with each other at the concave sides thereof when the electrodes 110a and 110b are at the closed position.

It should be noted, however, that the shape of the front portion 140 is not limited to that described above and may be formed in any shape including a rod like shape.

Each of the shafts 128 has a constant outer diameter except at the tip portion 128a. The tip portion 128a has a smaller diameter than the other portion or body 128b of the shaft 128.

The insulating block 130 is a single piece made of ceramic or hard resin such as poly-tetra-fluoro-ethylene, for example. The insulating block 130 has front and rear sides (150, 152) and right and left sides (154, 156). The insulating block 130 is located within the slit 124 of the supporting member 120 such that the right and left sides (154, 156) face the right and left inner side surfaces 124a and 124b of the slit 124, respectively.

Two through holes 158a and 158b are formed to the insulating block 130 so as to be perpendicular to the right and left sides 154 and 156 of the insulating block 130. The insulating block 130 is mounted to the supporting member 120 by inserting the pair of shafts 128 through the first and second through holes 158a and 158b, respectively. Since the insulating block 130 is supported by two shafts 128, it does not rotate within the slit 124.

It should be noted that each of the through holes 158a and 158b has an inner diameter slightly smaller than the outer diameter of the body of each shaft 128. Accordingly, the shafts 128 tightly fit into the respective through holes 158a and 158b.

FIGS. 7A and 7B show the right side 154 and the rear side 156 of the insulating block 130, respectively. Further, FIG. 8 is a sectional view of the electrode assembly 109 taken along a line VIII-VIII in FIG. 4.

The insulating block 130 has substantially the same width W as the slit 124. The right side 154 of the insulating block 130 is deformed to define a first stepped back surface 154a. Similarly, the left side 156 of the insulating block 130 is deformed to define a second stepped back surface 156a.

As shown in FIG. 8, first and second stepped back surfaces 154a and 156a contribute to form first and second spaces 170a and 170b between the insulating block 130 and the arms 122 of the supporting member 120 for receiving the first and second electrodes 110a and 110b, respectively. The first and second stepped back surface 154a and 156a are formed such that one of the shafts 128 penetrates the first space 170a but does not expose to the second space 170b while the other one penetrates the second space 170b but does not expose to the first space 170a.

The first and second electrodes 110a and 110b are pivotably mounted to the shafts 128 within the first and second spaces 170a and 170b, respectively.

The first and second stepped back surfaces 154a and 156a are formed such that the widths of the first and second spaces 170a and 170b become slightly larger than the widths of the first and second electrode 110a and 110b, respectively.

As shown in FIG. 8, each of the arms 122 of the supporting member 120 is provided with two through holes (160a, 160b, 160c and 160d). The through holes 160b and 160d are formed to receive the tip portion 128a of the shaft 128. The inner diameters of the through holes 160b and 160d are smaller that the outer diameter of the body 128b of the shaft 128 but slightly larger than the tip portion 128a. The through holes 160a and 160c are formed to have an inner diameter slightly larger than the outer diameter of the body 128b of the shaft 128. By inserting the shafts 128 as above, the first and second electrodes 110a and 110b are coupled to the supporting member 120 with the insulating block 130 being placed therebetween.

One of the shaft 128 is inserted, from the tip portion 128a thereof, into the through hole 160a, the supporting hole 144 of the second electrode 110b, the through hole 158b of the insulating block 130 and the through hole 160b of the supporting member 120. The other shaft 128 is inserted, from the tip portion thereof, into the through hole 160c, the supporting hole 144 of the first electrode 110a, the through hole 158a of the insulating block 130 and the through hole 160d.

As previously mentioned, the inner diameter of each of the through holes 158a and 158b of the insulating block 130 is slightly smaller than the outer diameter of the body 128b of the shaft 128. Thus, the shafts 128 are pressed into the insulating block 130. The shafts 128 tightly fitted into the insulating block 130 does not come off from the insulating block 130 and hence from the electrode assembly 109, and thereby prevents the electrode assembly 109 from disassembling. It is not necessary to swage the end portions of the shafts 128 or apply adhesions to the shafts 128 to fix the shafts 128 to the electrode assembly 109. It should be noted, however, that the end portions of the shafts may be also additionally swaged.

In the treatment tool 100 configured as above, the first and second electrodes 110a and 110b does not come into contact with each other except when the first and second electrodes 110a and 110b are moved to the closed position since the insulating block 130 is located between the first and second electrode 110a, 110b.

Further, the insulating block 130 supports the shafts 128 passed through the through holes 158a and 158b to prevent the shafts 128 from being bent and/or broken by the force exerted thereon from the first and second electrodes 110a and 110b as the first and second electrodes 110a and 110b are moved between the open and closed positions.

Further, since the insulating block 130 has substantially the same width as the slit 124, the arms 122 having the insulating block 130 therebetween do not bend inwardly even if external force is exerted on the arms 122, and hence the arms 122 do not make the first and second electrodes 110a and 110b immovable between the open and closed positions by strongly pressing them.

The insertion portion 104 of treatment tool 100 configured as above is introduced into a body cavity such as a stomach through an endoscope and the first and second electrodes 110a and 110b are located in the vicinity of a target portion of the mucosa.

Then, the operation portion 102 of the treatment tool 100 is operated such that the pair of conductive wires 108 is slid forwards within the sheath 106 and swing the first and second electrodes 110a and 110b to the open position. Then, the electrodes 110a and 110b are moved by the endoscope such that the target portion of the mucosa is located between the electrodes 110a and 110b.

Next, the pair of conductive wires 108 are retracted by pulling back the rod portion 114 with respect to the cylindrical portion 112 to move the front portions 140 of the electrodes 110a and 110b to the closed position and thereby grasping the target mucosa.

Next, a high frequency electrical power is supplied from the power supply 200 to the first and second electrodes 110a and 110b via the conductive wires 108. As a result, a high frequency current flows through the mucosa placed between the electrodes 110 and coagulates the mucosa.

While the invention has been described with particular reference to its preferred embodiments, it will be understood by those skilled in the art that various changes may be made and equivalents may be substituted for elements of the preferred embodiments without departing from the invention. In addition, many modifications may be made to adapt a particular situation and material to a teaching of the present invention without departing from the essential teachings of the invention.

For example, the shaft 128 may be formed such that the end portion opposite to the tip portion 128a has a larger diameter than the body 128b so as to prevent the shaft 128 from passing through the through holes 160a or 160c of the supporting member 120.

Further, the first and second electrodes 110a and 110b may be also pivotably mounted on a common shaft instead of being mounted on different shafts.

The present disclosure relates to the subject matter contained in Japanese Patent Application No. P2002-207777, filed on Jul. 17, 2002, which is expressly incorporated herein by reference in its entirety.

What is claimed is:

1. A treatment tool configured to be inserted into a human body through an endoscope, comprising:
    an elongated inserting portion configured to be inserted through an accessory channel of the endoscope;
    a supporting member attached to a distal end of said inserting portion, said supporting member being provided with a slit;
    a shaft attached to said supporting member so as to cross said slit in a width direction thereof;
    a pair of manipulation members, at least one of said pair of manipulation members being pivotably supported for movement by said shaft within said slit so as to open and close with respect to another of said pair of manipulation members, said pair of manipulation members comprising a pair of electrodes connectable to a high frequency power supply, said manipulation members being movable between opened and closed positions via leads connected to said high frequency power supply; and
    a spacer located between said pair of manipulation members, said spacer insulating said electrodes from each other, and remaining stationary with respect to said supporting member during movement of the manipulation member,
    wherein said shaft is supported by said spacer so as not to come off from said supporting member.

2. The treatment tool according to claim 1, wherein said shaft is pressed into said spacer.

3. The treatment tool according to claim 2, wherein said spacer is provided with a through hole having an inner diameter smaller than an outer diameter of said shaft, said shaft being pressed into said through hole.

4. The treatment tool according to claim 1, comprising a pair of said shafts, both of said shafts being pressed into said spacer, each of said pair of manipulation members being pivotably mounted to respective one of said shafts so as to open and close.

5. The treatment tool according to claim 4, wherein said spacer is provided with a pair of through holes formed in parallel to each other, each of said through holes having an inner diameter smaller than an outer diameter of each of said shafts, said shafts being pressed into respective one of said through holes.

6. The treatment tool according to claim 1, wherein said spacer comprises poly-tetra-fluoro-ethylene.

7. The treatment tool according to claim 1, wherein said spacer comprises ceramic.

8. The treatment tool according to claim 1, wherein said supporting member comprises insulating material.

9. The treatment tool according to claim 8, wherein said supporting member comprises rigid plastic.

10. The treatment tool according to claim 8, wherein said supporting member comprises ceramics.

11. The treatment tool according to claim 1, wherein said shaft engages said supporting member, said spacer and one of said manipulation members.

12. The treatment tool according to claim 1, wherein said pair of manipulation members are configured to rotate about said shaft.

13. The treatment tool according to claim 1, further comprising a second shaft, each of said shafts engaging one of said manipulation members and said spacer.

14. The treatment tool according to claim 13, each said shaft further engaging said supporting member at each side of said slit.

15. A treatment tool configured to be inserted into a human body through an endoscope, said treatment tool comprising:
    an elongated insertion portion configured to be inserted through an accessory channel of the endoscope;
    a supporting member attached to a distal end of said inserting portion, said supporting member having a longitudinally extending slit;
    a shaft attached to said supporting member so as to extend across said slit in a width-wise direction;
    a manipulation member, pivotally supported by said shaft so as to pivot about said shaft between opened and closed positions with respect to another manipulation member;
    a spacer that remains stationary with respect to said support member during pivoting of said manipulation member, said spacer located between said manipulation member and said another manipulation member and supporting said shaft; and
    power conductors connected to each said manipulation member and said another manipulation member, said power conductors configured to supply power to said electrodes and to pivotally move said manipulation member and said another manipulation member.

16. The treatment tool according to claim 15, said manipulation member and said another manipulation member comprising conductive electrodes.

17. The treatment tool according to claim 1, said spacer being configured to have a width corresponding to a width of said slit.

18. The treatment tool according to claim 15, said spacer being configured to have a width corresponding to a width of said slit.

19. The treatment tool according to claim 1, one of the leads being connected to a positive terminal of said high frequency power supply and the other of the leads being connected to a negative terminal of said high frequency power supply.

20. The treatment tool according to claim 15, one of the power conductors being connected to a positive terminal of a power supply and the other of the power conductors being connected to a negative terminal of the power supply.

21. The treatment tool according to claim 1, said at least one of said pair of manipulation members being movable between the open and closed positions by pivotal motion about said shaft.

* * * * *